US011078179B2

(12) United States Patent
Saigusa et al.

(10) Patent No.: US 11,078,179 B2
(45) Date of Patent: Aug. 3, 2021

(54) METHOD FOR PRODUCING CYCLIC ESTER

(71) Applicant: Kureha Corporation, Tokyo (JP)

(72) Inventors: Nanako Saigusa, Tokyo (JP); Takenori Tose, Tokyo (JP); Toshihiko Ono, Tokyo (JP); Yoshinori Suzuki, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 16/975,214

(22) PCT Filed: Mar. 7, 2019

(86) PCT No.: PCT/JP2019/009026
§ 371 (c)(1),
(2) Date: Aug. 24, 2020

(87) PCT Pub. No.: WO2019/172361
PCT Pub. Date: Sep. 12, 2019

(65) Prior Publication Data
US 2020/0392102 A1 Dec. 17, 2020

(30) Foreign Application Priority Data
Mar. 7, 2018 (JP) ................................. 2018-041327

(51) Int. Cl.
*C08F 2/00* (2006.01)
*C08G 85/00* (2006.01)
*C08G 61/04* (2006.01)
*C07D 319/12* (2006.01)

(52) U.S. Cl.
CPC ......... *C07D 319/12* (2013.01); *C08J 2335/02* (2013.01); *C08J 2467/04* (2013.01)

(58) Field of Classification Search
CPC .... C07D 319/12; C07B 61/00; C08J 2467/04; C08J 2335/02
USPC ................................................. 526/71; 520/1
See application file for complete search history.

(56) References Cited

U.S. PATENT DOCUMENTS

| 5,830,991 | A | * | 11/1998 | Shiiki | .................. | C07D 319/12 |
|---|---|---|---|---|---|---|
| | | | | | | 549/267 |
| 2003/0191326 | A1 | | 10/2003 | Yamane et al. | | |
| 2011/0263875 | A1 | | 10/2011 | Suzuki et al. | | |
| 2012/0289713 | A1 | | 11/2012 | Suzuki et al. | | |
| 2015/0025126 | A1 | | 1/2015 | Davis et al. | | |
| 2016/0002196 | A1 | | 1/2016 | Ikeyama et al. | | |

FOREIGN PATENT DOCUMENTS

| CN | 101495440 | | * | 7/2009 | | |
|---|---|---|---|---|---|---|
| CN | 102712617 | A | | 10/2012 | | |
| EP | 2 377 858 | A1 | | 10/2011 | | |
| GB | 2 331 986 | A | | 6/1999 | | |
| JP | 9-328481 | A | | 12/1997 | | |
| JP | 2003-292486 | A | | 10/2003 | | |
| JP | 2012-140383 | A | | 7/2012 | | |
| WO | 02/14303 | A1 | | 2/2002 | | |
| WO | WO2002014303 | | * | 2/2002 | | |
| WO | 2010/073512 | A1 | | 7/2010 | | |
| WO | WO-2010073512 | A1 | * | 7/2010 | ........... | C07D 319/12 |
| WO | 2011/089802 | A1 | | 7/2011 | | |
| WO | WO-2011089802 | A1 | * | 7/2011 | ........... | C07D 319/12 |
| WO | 2014/157140 | A1 | | 10/2014 | | |

OTHER PUBLICATIONS

Yamane et al, WO 2002/014303 Machine Translation, Feb. 21, 2002 (Year: 2002).*
Ogawa et al, CN 101495440 Machine Translation, Jul. 29, 2009 (Year: 2009).*
Suzuki et al, WO 2010073512 Machine Translation, Jul. 1, 2010 (Year: 2010).*
Suzuki et al, WO 2011089802 Machine Translation, Jul. 28, 2011 (Year: 2011).*
International Preliminary Report on Patentability (Chapter I) of the International Preliminary Examining Authority for PCT/JP2019/009026 dated Sep. 8, 2020.
English translation of International Preliminary Report on Patentability (Chapter I) of the International Preliminary Examining Authority for PCT/JP2019/009026 dated Sep. 8, 2020.
International Search Report of the International Searching Authority for PCT/JP2019/009026 dated May 21, 2019.
English translation of International Search Report of the International Searching Authority for PCT/JP2019/009026 dated May 21, 2019.
Written Opinion of the International Searching Authority for PCT/JP2019/009026 dated May 21, 2019.
English translation of Written Opinion of the International Searching Authority for PCT/JP2019/009026 dated May 21, 2019.
Notification of Reason for Refusal of the Intellectual Property Office of Japan for JP 2020-505101 dated Jun. 16, 2020, including its English language translation.
Office Action dated Jan. 22, 2021, in Chinese Patent Application No. 201980012566.7.

(Continued)

*Primary Examiner* — Jessica Whiteley
(74) *Attorney, Agent, or Firm* — Birch, Stewart, Kolasch & Birch, LLP

(57) ABSTRACT

In a method for producing a cyclic ester according to an embodiment of the present invention, a mixture (I) containing an aliphatic polyester, a specific polyalkylene glycol diether, and a sulfonic acid compound as a thermal stabilizer is prepared and heated in predetermined conditions to obtain a mixture (II) in a state of solution. Furthermore, heating of the mixture (II) is continued to distill, together with the polyalkylene glycol diether, a cyclic ester formed by the depolymerization reaction, and thus a distillate (III) is obtained. The cyclic ester is recovered from the distillate (III). At this time, a specific solubilizing agent is added to at least one of the mixture (I) or (II). In this production method, the sulfonic acid compound as the thermal stabilizer is contained in the mixtures (I) and (II) and the distillate (III).

4 Claims, 3 Drawing Sheets

(56) References Cited

OTHER PUBLICATIONS

Extended European Search Report dated Apr. 1, 2021, in European Patent Application No. 19764301 8.
Office Action dated Apr. 21, 2021, in Chinese Patent Application No. 201980012566.7.

* cited by examiner

METHOD FOR PRODUCING CYCLIC ESTER

TECHNICAL FIELD

The present invention relates to a method for producing a cyclic ester, and more specifically relates to a method for producing a cyclic ester, which has excellent production efficiency while formation of by-products is suppressed.

BACKGROUND ART

In Patent Document 1, a method for producing a cyclic ester by depolymerizing an aliphatic polyester is known. Furthermore, in Patent Document 2, to enhance solubility of an α-hydroxycarboxylic acid oligomer in a method for producing a cyclic ester of an α-hydroxycarboxylic acid dimer, use of a solubilizing agent is known. Furthermore, Patent Document 3 describes that a solubilizing agent is required to be used in a method for producing glycolide by depolymerization of a glycolic acid oligomer a solution phase. However, in Patent Documents 2 and 3, specific compound names relating to sulfones or sulfonic acids are not described. In addition, there is no description on the effect of reducing amounts of by-products contained in the glycolide produced by addition of the sulfones or sulfonic acids. Patent Document 4 describes a method for producing glycolide, which enhances the purity of the resulting glycolide by using, as a depolymerization raw material, a glycolic acid oligomer having a terminal carboxyl group concentration of 400 eq/t or less.

CITATION LIST

Patent Document

Patent Document 1: WO 2002/014303
Patent Document 2: JP 9-328481 A
Patent Document 3: WO 2010/073512
Patent Document 4: WO 2014/157140

SUMMARY OF INVENTION

Technical Problem

Methods for producing a cyclic ester in the related art have problems that a large quantity of impurity is contained in the glycolide distilled by depolymerization.

An object of the present invention is to provide a method for producing a cyclic ester, which has excellent production efficiency while formation of by-products is suppressed.

Solution to Problem

As a result of diligent research to solve the problems described above, the present inventors found that use of a sulfonic acid compound as a thermal stabilizer can suppress formation of by-products to be contained in a cyclic ester and improve production efficiency of the cyclic ester, and thus completed the present invention.

That is, an embodiment of the present invention is a method for producing a cyclic ester, comprising:
a step (I) of preparing a mixture (I) containing
an aliphatic polyester,
a polyalkylene glycol diether represented by Formula (1) below and having a boiling point from 230 to 450° C. and a molecular weight from 150 to 450,

[Chemical Formula 1]

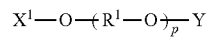

(1)

where, $R^1$ represents a methylene group or a linear or branched alkylene group having from 2 to 8 carbons, $X^1$ represents a hydrocarbon group, Y represents an alkyl group having from 2 to 20 carbons or an aryl group, p represents an integer of 1 or greater, and in a case where p is 2 or greater, a plurality of $R^1$ moieties may be the same or different, and
a thermal stabilizer;
a step (II) of producing a mixture (II) in a state of solution by heating the mixture (I) under normal pressure or reduced pressure to a temperature at which depolymerization reaction of the aliphatic polyester starts;
a step (III) of producing a distillate (III) by continuing the heating of the mixture (II) and distilling a cyclic ester formed by the depolymerization reaction together with the polyalkylene glycol diether, and
a step (IV) of recovering the cyclic ester from the distillate (III);
a polyalkylene glycol monoether represented by Formula (2) below being added to at least one of the mixture (I) or the mixture (II) as a solubilizing agent to enhance solubility of the aliphatic polyester in the polyalkylene glycol diether,

[Chemical Formula 2]

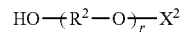

(2)

where, $R^2$ represents a methylene group or a linear or branched alkylene group having from 2 to 8 carbons, $X^2$ represents a hydrocarbon group, r represents an integer of 1 or greater, and in the case where r is 2 or greater, a plurality of $R^2$ moieties may be the same or different; and
the thermal stabilizer being a sulfonic acid compound, and the distillate (III) also containing the sulfonic acid compound which is the thermal stabilizer.

Advantageous Effects of Invention

According to the method for producing a cyclic ester according to an embodiment of the present invention, production efficiency can be enhanced while formation of by-products to be contained in the cyclic ester is suppressed.

DESCRIPTION OF EMBODIMENTS

Figure 1:
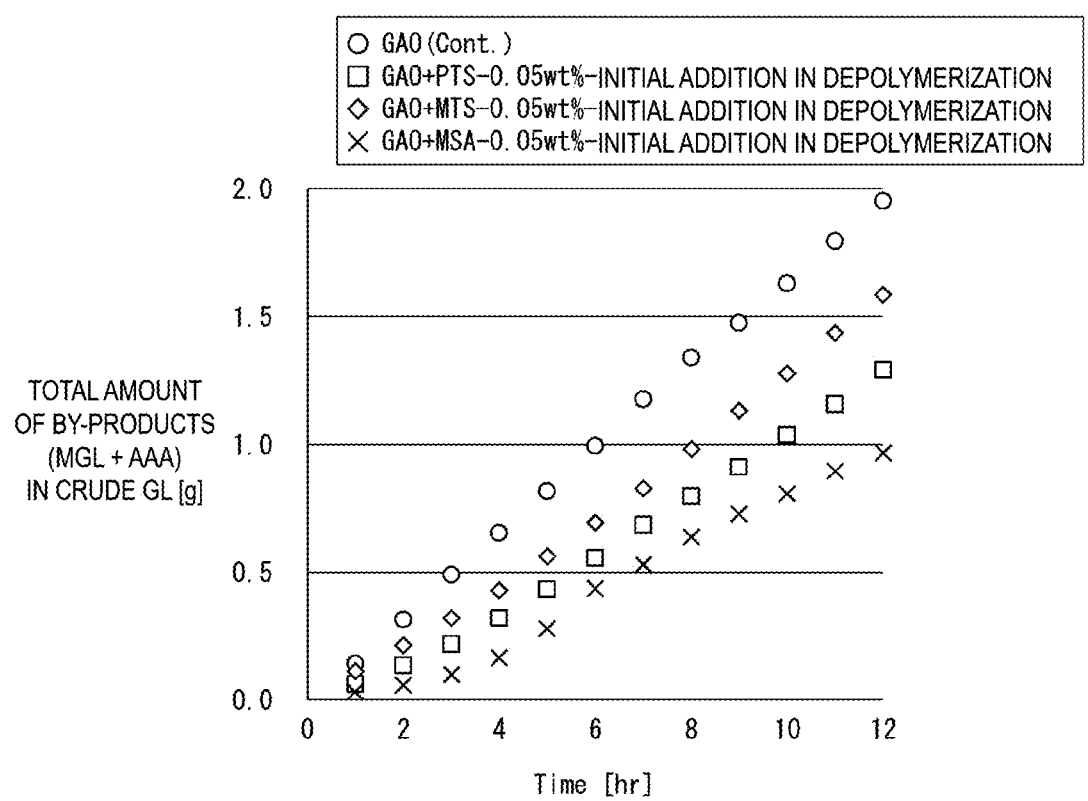
FIG. 1 is a graph showing a total amount of by-products (MGL+AAA) in a crude glycolide as a function of depolymerization reaction time.

The method for producing a cyclic ester according to an embodiment of the present invention includes the steps (I) to (IV), and the distillate (III) obtained by the step (III) also contains the sulfonic acid compound which is a thermal stabilizer. The steps (I) to (IV) are described in detail below.

Step (I)

In the step (I), a mixture (I) is prepared which contains an aliphatic polyester, a polyalkylene glycol diether represented by Formula (1) below and has a boiling point from 230 to 450° C. and a molecular weight from 150 to 450,

[Chemical Formula 3]

(1)

and a sulfonic acid compound as a thermal stabilizer. First, a compound used in the step (I) is described.

Aliphatic Polyester

The aliphatic polyester used in the present embodiment is a (co)polymer containing a repeating unit that can form a cyclic ester by depolymerization. Such an aliphatic polyester can be obtained by ring-opening (co)polymerization using a cyclic ester, such as glycolide, lactide, or lactones, as a monomer. Furthermore, such an aliphatic polyester can be also obtained by polycondensation of α-hydroxycarboxylic acid, such as glycolic acid and lactic acid, or an alkylester thereof or a salt thereof.

Specific examples of the aliphatic polyester include poly (α-hydroxycarboxylic acid), such as polyglycolic acids (including polyglycolide) and polylactic acids (including polylactide); polylactones, such as poly(ε-caprolactone); and copolyesters, such as ring-opened copolymers of two or more types of cyclic esters, copolymers of a cyclic ester and another comonomer, copolymers of two or more types of α-hydroxycarboxylic acids, and copolymers of α-hydroxycarboxylic acid and another comonomer.

Note that, in the present specification, the polyhydroxycarboxylic acid includes not only poly(α-hydroxycarboxylic acid) but also polylactones as long as they are aliphatic polyesters having a repeating unit of "hydroxycarboxylic acid" (—O —R—CO—). Furthermore, for example, polyglycolic acid and polylactic acid are referred to as poly(α-hydroxycarboxylic acid) even when they are ring-opened polymers of dimeric cyclic esters as well as polymers obtained by polycondensation of α-hydroxycarboxylic acid.

Furthermore, in the present specification, definition of the aliphatic polyester includes from low molecular weight materials, such as oligomers, to high molecular weight materials. The low molecular weight aliphatic polyester, such as oligomer, and the high molecular weight aliphatic polyester are not necessarily clearly distinguished.

However, in the present specification, an oligomer or a low molecular weight aliphatic polyester such as oligomer are defined as a low molecular weight substance having a weight average molecular weight of less than 10000 and, in many cases, less than 5000. The degree of polymerization of the oligomer, that is, the number of repeating units of "hydroxycarboxylic acid" (—O—R—CO—), is typically 2 or greater, and preferably 5 or greater.

The high molecular weight aliphatic polyester has a weight average molecular weight of typically 10000 or greater, preferably from 10000 to 1000000, and more preferably from 20000 to 800000. This weight average molecular weight is a value measured by using gel permeation chromatography (GPC). For example, in the case of a poly(α-hydroxycarboxylic acid) such as polyglycolic acid (i.e. polyglycolide), the weight average molecular weight can be measured by GPC measurement, calibrated with polymethylmethacrylate (PMMA) standard, using hexafluoroisopropanol (HFIP) as a solvent.

As the aliphatic polyester, typically, a polyhydroxycarboxylic acid having a repeating unit of hydroxycarboxylic acid is used. Among these, poly(α-hydroxycarboxylic acid), such as polyglycolic acid (i.e. polyglycolide) and polylactic acid (i.e. polylactide), is more preferred, and a polyglycolic acid is particularly preferred. The aliphatic polyester may be a copolymer, and in this case, a copolymer having a content of a repeating unit of α-hydroxycarboxylic acid, such as glycolic acid and lactic acid, of 50 wt % or greater is preferred.

Each aliphatic polyester can be synthesized in accordance with an ordinary method. For example, a low molecular weight substance, such as an α-hydroxycarboxylic acid oligomer, can be obtained by subjecting α-hydroxycarboxylic acid or an alkylester thereof (alkyl group having approximately from 1 to 4 carbons) or a salt thereof to polycondensation in the presence of a catalyst, as necessary.

More specifically, for example, to synthesize a glycolic acid oligomer used as a starting raw material of glycolide, glycolic acid or an ester thereof or a salt thereof is heated to a temperature from 100° C. to 250° C., preferably from 140° C. to 230° C., under reduced pressure or under pressure in the presence of, as necessary, a condensation catalyst or a transesterification catalyst, and a condensation reaction or a transesterification reaction is performed until substantially no low molecular weight substances, such as water and alcohol, are distilled. After the condensation reaction or the transesterification reaction is complete, the produced oligomer can be used as is as a raw material. The obtained oligomer may be extracted from the reaction system, washed with a nonsolvent such as benzene or toluene, and used after unreacted matter, the catalyst, and the like are removed. The structure of the oligomer may be cyclic or linear. Other α-hydroxycarboxylic acid oligomer may also be synthesized with the same method.

The oligomer may have a low degree of polymerization, but the melting point (Tm) is typically 140° C. or higher, preferably 160° C. or higher, and more preferably 180° C. or higher, from the perspective of the yield of cyclic ester, such as glycolide, at the time of depolymerization. Here, Tm is the melting point detected when heated at a rate of 10° C./min in an inert gas atmosphere, using a differential scanning calorimeter (DSC).

A high molecular weight aliphatic polyester can be synthesized by ring-opening (co)polymerization of glycolide, lactide, or lactones. Furthermore, as a high molecular weight aliphatic polyester, a waste of a used product, a formed layer, or the like can be suitably used, and thereby, recycling can be achieved. The shape of the high molecular weight aliphatic polyester is not particularly limited, and any shapes such as a sheet shape, a film shape, a thread shape, a spherical shape, or a rod shape can be used. It is preferable from the perspective of increasing the reaction efficiency to prepare the high molecular weight aliphatic polyester into a granular shape, a powder, or a fiber shape, or the like prior to a depolymerization reaction. For this purpose, the products can be used in a depolymerization reaction after being granulated or powderized by pulverization, melting, or the like or processed into a fiber shape by melting or drawing.

The aliphatic polyester may be added all together to a reaction vessel before the reaction, or may be added during the reaction by continuous addition or batch addition or by a combination of these.

In the present embodiment, the aliphatic polyester is preferably obtained by performing a condensation reaction of a sulfonic acid compound and α-hydroxycarboxylic acid at a temperature from 100 to 250° C., preferably from 150 to 230° C., and more preferably from 170 to 220° C., under normal pressure or reduced pressure. Consequently, the sulfonic acid compound contained in the reaction product after the condensation reaction can be used as is as a sulfonic acid compound being a thermal stabilizer in the following step (I).

Polyalkylene Glycol Diether

Next, the polyalkylene glycol diether used in the present embodiment is described.

The polyalkylene glycol diether according to the present embodiment is represented by Formula (1) below.

[Chemical Formula 4]

(1)

In Formula (1), $R^1$ represents a methylene group or a linear or branched alkylene group having from 2 to 8 carbons, $X^1$ represents a hydrocarbon group, Y represents an alkyl group having from 2 to 20 carbons or an aryl group, p is an integer of 1 or greater, and when p is 2 or greater, a plurality of $R^1$ moieties may be the same or different.

The boiling point of the polyalkylene glycol diether of the present embodiment is from 200 to 450° C., preferably from 200 to 450° C., more preferably from 220 to 430° C., and most preferably from 230 to 420° C. When the boiling point of the polyalkylene glycol diether is in this range, the polyalkylene glycol diether tends to be distilled, and distillation with the cyclic ester formed by the depolymerization reaction is facilitated.

Furthermore, the molecular weight of the polyalkylene glycol diether of the present embodiment is from 150 to 450, preferably from 180 to 420, and more preferably from 200 to 400. By setting the molecular weight to this range, codistillation of the polyalkylene glycol diether and the cyclic ester is facilitated.

In the polyalkylene glycol diether, the ether groups ($X^1$ and Y) at the both terminals are both alkyl groups, and the total number of carbons of the alkyl groups contained in the ether groups at the both terminals is from 3 to 21, and more preferably from 6 to 20. Examples of such an alkyl group include a propyl group, a butyl group, a pentyl group, a hexyl group, a heptyl group, an octyl group, a nonyl group, a decyl group, and a lauryl group. These alkyl groups may be linear or branched.

As the polyalkylene glycol dialkyl ether, polyethylene glycol dialkyl ether is preferred. Among these, diethylene glycol dialkyl ether, triethylene glycol dialkyl ether, and tetraethylene glycol dialkyl ether are more preferred.

As the alkyl groups of the ether groups at the both terminals of the polyalkylene glycol diether, the alkly groups having the same number of carbons, such as dibutyl, dihexyl, or dioctyl, can be used, but the number of the carbons does not necessarily need to be the same. Therefore, for example, a combination of different types of alkyl groups, such as a propyl group and a lauryl group, a hexyl group and a heptyl group, or a butyl group and an octyl group, may be employed.

In the case where Y in Formula (1) is an aryl group, the number of carbons of the aryl group is from 1 to 30, preferably from 2 to 25, and more preferably from 6 to 20. Specific examples of the aryl group include a phenyl group, a naphthyl group, a substituted phenyl group, and a substituted naphthyl group. The substituent is preferably an alkyl group, an alkoxy group, or a halogen atom (such as chlorine, bromine, or iodine). In the case of a substituted phenyl group, the number of substituents is typically from 1 to 5, and preferably from 1 to 3. In the case a plurality of the substituents are present, the substituents may be the same or different.

In Formula (1), the alkyleneoxy unit (—$R^1$—O—) is not particularly limited as long as $R^1$ is a methylene group or a linear or branched alkylene group having from 2 to 8 carbons. Specific examples thereof include polyethylene glycol ethers containing ethyleneoxy units in which $R^1$ has 2 carbons, polypropylene glycol ethers containing propyleneoxy units in which $R^1$ has 3 carbons, and polybutylene glycol ethers containing butyleneoxy units in which $R^1$ has 4 carbons. Among these, from the perspectives of availability of raw materials and ease in synthesis, a polyethylene glycol ether is particularly preferred.

When the number of repetitions p of the alkyleneoxy unit (—$R^1$—O—) is 2 or greater, a plurality of $R^1$ moieties may be the same or different from one another. Examples of substances in which a plurality of $R^1$ moieties are different from each other include substances containing ethyleneoxy units and propyleneoxy units obtained by mixing and reacting ethylene oxide and propylene oxide, but are not limited thereto.

Specific examples of such a polyalkylene glycol diether include polyethylene glycol dialkyl ethers, such as diethylene glycol dibutyl ether, diethylene glycol dihexyl ether, diethylene glycol dioctyl ether, triethylene glycol dibutyl ether, triethylene glycol dihexyl ether, triethylene glycol dioctyl ether, tetraethylene glycol dibutyl ether, tetraethylene glycol dihexyl ether, tetraethylene glycol dioctyl ether, diethylene glycol butylhexyl ether, diethylene glycol butyloctyl ether, diethylene glycol hexyloctyl ether, triethylene glycol butylhexyl ether, triethylene glycol butyloctyl ether, triethylene glycol hexyloctyl ether, tetraethylene glycol butylhexyl ether, tetraethylene glycol butyloctyl ether, and tetraethylene glycol hexyloctyl ether; polyalkylene glycol dialkyl ether in which the ethyleneoxy unit in the polyethylene glycol dialkyl ether is substituted with a propyleneoxy unit or a butyleneoxy unit, such as polypropylene glycol dialkyl ether and polybutylene glycol dialkyl ether; diethylene glycol butylphenyl ether, diethylene glycol hexylphenyl ether, diethylene glycol octylphenyl ether, triethylene glycol butylphenyl ether, triethylene glycol hexylphenyl ether, triethylene glycol octylphenyl ether, tetraethylene glycol butylphenyl ether, tetraethylene glycol hexylphenyl ether, tetraethylene glycol octylphenyl ether, or polyethylene glycol alkylaryl ether in which at least one hydrogen atom in the phenyl group of these compounds is substituted with alkyl group(s), alkoxy group(s), or halogen atom(s); polyalkylene glycol alkylaryl ether in which the ethyleneoxy unit of the polyethylene glycol alkylaryl ether is substituted with a propyleneoxy unit or a butyleneoxy unit, such as polypropylene glycol alkylaryl ether and polybutylene glycol alkylaryl ether; polyethylene glycol diaryl ether, such as diethylene glycol diphenyl ether, triethylene glycol diphenyl ether, tetraethylene glycol diphenyl ether, or compounds in which at least one hydrogen atom of the phenyl group of these compounds is substituted with an alkyl group, an alkoxy group, a halogen atom, or the like; and polyalkylene glycol diaryl ether in which an ethyleneoxy unit in these polyethylene glycol diaryl ether is substituted with a propyleneoxy unit or a butyleneoxy unit, such as polypropylene glycol diaryl ether and polybutylene glycol diaryl ether.

For the polyalkylene glycol diether, the proportion of the total amount of the amount remained in the reaction solution after the depolymerization reaction is performed and the amount recovered from the distillate relative to the charged amount (i.e. recovery rate) is preferably 85% or greater, more preferably 90% or greater, and even more preferably 95% or greater.

The polyalkylene glycol diether preferably has a solubility of cyclic ester, such as glycolide, of 0.1% or greater at 25° C. In many cases, a polyalkylene glycol diether having a solubility of cyclic ester in a range of 0.1 to 10% is preferred. Note that the solubility of the cyclic ester at 25° C. represents a percentage of the mass B (g) of the cyclic ester relative to the volume A (mL) of the polyalkylene glycol diether at the time when the cyclic ester, such as glycolide, is dissolved to saturation in the polyalkylene glycol diether at 25° C. That is, the solubility is represented by the following equation.

Solubility (%)=($B/A$)×100

For example, the polyalkylene glycol diether can be produced by etherification of a terminal hydroxy group of an alkylene glycol monoether obtained by adding an alcohol to an alkylene oxide or a polyalkylene glycol monoether obtained by polyaddition. At this time, the etherification may be performed by a known method, and the method is not particularly limited. Examples of a common method of etherification include a method that allows a polyalkylene glycol monoether to react with an alkyl halide in the presence of metallic sodium, sodium hydride, or sodium hydroxide; a method that allows sodium iodide to coexist in that reaction; and a method that uses, as an alkylating agent, a substance obtained by subjecting an alcohol to sulfonic acid esterification using sulfonic acid chloride (e.g. tosyl chloride, methyl chloride) instead of alkyl halide (i.e. alkylating agent) in the presence of a basic compound.

Thermal Stabilizer

In the present embodiment, a sulfonic acid compound is used as a thermal stabilizer. Specific examples of the sulfonic acid compound as a thermal stabilizer include p-toluene sulfonic acid (PTS), methyl p-toluenesulfonate (MTS), methanesulfonic acid (MSA), butyl p-toluenesulfonate, hexyl p-toluenesulfonate, naphthalenesulfonic acid, dodecylbenzenesulfonic acid, 4-ethylbenzenesulfonic acid, 2-naphthalenesulfonic acid, and 4-hydroxybenzenesulfonic acid. One type or two or more types selected from the group consisting of these can be appropriately selected, mixed, and used. The sulfonic acid compound as the thermal stabilizer is preferably an organic sulfonic acid compound. Furthermore, the sulfonic acid compound as the thermal stabilizer is preferably a sulfonic acid compound having a high solubility in the polyalkylene glycol diether. Specifically, its solubility in the polyalkylene glycol diether is 0.04 mol/L or greater, preferably 0.09 mol/L or greater, more preferably 0.12 mol/L or greater, even more preferably 0.25 mol/L or greater, and particularly preferably 0.35 mol/L or greater. By setting the solubility of the sulfonic acid compound to the range described above, the production rate of cyclic ester can be further enhanced. Although the mechanism of action is not clear, it is conceived that, by using a sulfonic acid compound having a high solubility as a thermal stabilizer, uniform dispersion of a compound, which is contained in the aliphatic polyester and catalyzes a depolymerization reaction, in the polyalkylene glycol diether is promoted.

Note that the solubility described above is a theoretical value at 25° C. as determined by a theoretical calculation using a computational chemistry software. For example, the solubility of the sulfonic acid compound in the polyalkylene glycol diether can be determined by, after the surface charge of the sulfonic acid compound is calculated by a quantum calculation, estimating at an estimation temperature of 25° C. by applying COnductor like Screening MOdel for Realistic Solvents (COSMO-RS).

The amount of the sulfonic acid compound used as the thermal stabilizer relative to the amount of the aliphatic polyester is from 0.005 to 5 mass %, preferably from 0.01 to 3.0 mass %, more preferably from 0.02 to 1 mass %, even more preferably from 0.03 to 0.7 mass %, and most preferably from 0.05 to 0.5 mass %. Note that, in the present embodiment, the sulfonic acid compound as the thermal stabilizer may be added in the step (I). Alternatively, in the case where an aliphatic polyester obtained by adding a sulfonic acid compound during condensation reaction of α-hydroxycarboxylic acid is used, this sulfonic acid compound may be used as a sulfonic acid compound as the thermal stabilizer.

Depolymerization Catalyst

In the present embodiment, optionally, a compound that catalyzes the depolymerization reaction (depolymerization catalyst) can be used. The method of adding the depolymerization catalyst is not limited as long as the depolymerization catalyst is contained in the mixture (I). For example, when the aliphatic polyester is obtained by subjecting α-hydroxycarboxylic acid to condensation, the depolymerization catalyst can be contained in the aqueous α-hydroxycarboxylic acid solution. As the depolymerization catalyst, metals such as Na, Li, K, Be, Mg, Ca, Sr, Al, Ga, In, Sc, La, Cr, Co, Fe, Ti, Sn, Ni, Zn, Zr, Pb, Sb, Bi, Ru, Os, Rh, and Ir, metal salts, and metal complexes can be used. Fe, Ti, Sn, and Zr are particularly preferred.

Step (II)

Next, the step (II) is described. In the step (II), under normal pressure or reduced pressure, the mixture (I) is heated to a temperature at which the depolymerization reaction of the aliphatic polyester starts. More specifically, for example, the aliphatic polyester is charged in a reaction vessel in a melt state or a solid state, optionally after pulverized into an adequate grain size, and then the polyalkylene glycol and the thermal stabilizer are mixed.

The mixture (I) containing the aliphatic polyester, the polyalkylene glycol, and the sulfonic acid compound as the thermal stabilizer is heated to a temperature of typically 200° C. or higher, preferably 230° C. or higher, and more preferably 250° C. or higher. Thereby, a mixture (II) in a solution state in which all or most of the aliphatic polyester is dissolved in the polyalkylene glycol diether can be obtained.

The operation of melting and dissolution of the aliphatic polyester is preferably performed in an inert gas atmosphere, such as a nitrogen gas.

In the present embodiment, a solubilizing agent is added to at least one of the mixture (I) or the mixture (II). In the present embodiment, the solubilizing agent is added to enhance solubility of the aliphatic polyester in the polyalkylene glycol diether. Thereby, a melt phase of the aliphatic polyester and a liquid phase of the polyalkylene glycol diether form into a substantially homogeneous phase.

The solubilizing agent used in the present embodiment is specifically the polyalkylene glycol monoether represented by Formula (2) below.

[Chemical Formula 5]

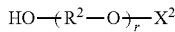
(2)

In Formula (2), $R^2$ represents a methylene group or a linear or branched alkylene group having from 2 to 8 carbons, $X^2$ represents a hydrocarbon group, r is an integer of 1 or greater, and when r is 2 or greater, a plurality of $R^2$ moieties may be the same or different.

Specific examples of the solubilizing agent used in the present embodiment include polyethylene glycol monoethers such as polyethylene glycol monomethyl ether, polyethylene glycol monopropyl ether, polyethylene glycol monobutyl ether, polyethylene glycol monohexyl ether, polyethylene glycol monooctyl ether, polyethylene glycol monodecyl ether, and polyethylene glycol monolauryl ether; polyalkylene glycol monoether, such as polypropylene glycol monoether and polybutylene glycol monoether, in which an ethyleneoxy group is substituted with a propyleneoxy group or a butyleneoxy group in the polyethylene glycol monoether. A polyethylene glycol monoether preferably has an alkyl group having from 1 to 8 carbons, and more preferably an alkyl group having from 6 to 18 carbons, as an ether group.

The amount of the solubilizing agent contained in at least one of the mixture (I) or the mixture (II) is typically from 30 to 5000 parts by mass, preferably from 50 to 2000 parts by mass, and more preferably from 60 to 200 parts by mass, per 100 parts by mass of the aliphatic polyester.

Step (III)

Next, the step (III) is described. In the step (III), heating of the mixture (II) in a solution state is continued, and the cyclic ester formed by the depolymerization reaction is distilled together with the polyalkylene glycol diether to obtain a distillate (III).

The heating temperature during the depolymerization reaction has only to be 200° C. or higher, at which the depolymerization of the aliphatic polyester occurs, but is preferably 200 to 320° C., more preferably 210 to 310° C., even more preferably from 220 to 300° C., and particularly preferably from 230 to 290° C.

The heating during the depolymerization reaction is performed under normal pressure or reduced pressure but is preferably performed under reduced pressure at 0.1 to 90 kPa. The pressure at this time is preferably from 1 to 50 kPa, more preferably from 3 to 30 kPa, and even more preferably from 5 to 20 kPa.

Step (IV)

Finally, the step (IV) is described. In the step (IV), the cyclic ester is recovered from the distillate (III). The cyclic ester contained in the distillate (III) can be easily separated and recovered by cooling the distillate (III) and optionally adding a nonsolvent of the cyclic ester.

According to the present embodiment, in addition to the mixture (I) and the mixture (II), the sulfonic acid compound being the thermal stabilizer is contained also in the distillate (III). Therefore, it is presumed that, since effects of suppressing side reactions during the depolymerization of the glycolic acid oligomer and suppressing decomposition of glycolide or the like are caused by the sulfonic acid compound as the thermal stabilizer, the content of by-products in the obtained cyclic ester, that is, glycolide, is reduced. Note that by-products in an embodiment of the present invention refer to "methyl glycolide (MGL)" and "acetoxyacetic acid (AAA)".

[Summary]

The method for producing a cyclic ester according to one aspect of the present invention is a method for producing a cyclic ester, comprising:

a step (I) of preparing a mixture (I) containing
an aliphatic polyester,
a polyalkylene glycol diether represented by Formula (1) below and having a boiling point from 230 to 450° C. and a molecular weight from 150 to 450,

[Chemical Formula 6]

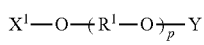
(1)

where, $R^1$ represents a methylene group or a linear or branched alkylene group having from 2 to 8 carbons, $X^1$ represents a hydrocarbon group, Y represents an alkyl group having from 2 to 20 carbons or an aryl group, p is an integer of 1 or greater, and when p is 2 or greater, a plurality of $R^1$ moieties may be the same or different; and a thermal stabilizer;

a step (II) of producing a mixture (II) in a state of solution by heating the mixture (I) under normal pressure or reduced pressure to a temperature at which depolymerization reaction of the aliphatic polyester starts;

a step (III) of producing a distillate (III) by continuing the heating of the mixture (II) and distilling a cyclic ester formed by the depolymerization reaction together with the polyalkylene glycol diether, and a step (IV) of recovering the cyclic ester from the distillate (III);

a polyalkylene glycol monoether represented by Formula (2) below being added to at least one of the mixture (I) or the mixture (II) as a solubilizing agent to enhance solubility of the aliphatic polyester in the polyalkylene glycol diether,

[Chemical Formula 7]

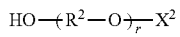
(2)

where, $R^2$ represents a methylene group or a linear or branched alkylene group having from 2 to 8 carbons, $X^2$ represents a hydrocarbon group, r represents an integer of 1 or greater, and in the case where r is 2 or greater, a plurality of $R^2$ moieties may be the same or different; and the thermal stabilizer being a sulfonic acid compound, and the distillate (III) also containing the sulfonic acid compound which is the thermal stabilizer.

In an aspect of the present invention, in the step (I), the thermal stabilizer may be a sulfonic acid compound added in a proportion from 0.005 to 5.0 mass % relative to an amount of the aliphatic polyester.

In an aspect of the present invention, the thermal stabilizer may be a sulfonic acid compound used during preparation of the aliphatic polyester by heating an α-hydroxycarboxylic acid at a temperature of 100 to 250° C. under normal pressure or reduced pressure to perform a condensation reaction.

Furthermore, in an aspect of the present invention, the mixture (I) further contains a depolymerization catalyst, and solubility of the thermal stabilizer in the polyalkylene glycol diether is 0.25 mol/L or greater.

Embodiments of the present invention will be described in further detail hereinafter using examples. The present invention is not limited to the examples below, and it goes without saying that various aspects are possible with regard to the details thereof. Furthermore, the present invention is not limited to the embodiments described above, and various modifications are possible within the scope indicated in the claims. Embodiments obtained by appropriately combining the technical means disclosed by the embodiments are also included in the technical scope of the present invention. In addition, all of the documents described in the present specification are herein incorporated by reference.

EXAMPLES

Preparation Example

Preparation of Glycolic Acid Oligomer

In an autoclave having a volume of 20 L, 20 kg of an industrial grade 70% glycolic acid aqueous solution (available from The Chemours Company Fc, Llc) was charged. Next, the mixture was heated under stirring at normal pressure to increase the temperature from room temperature to 210° C., and a polycondensation reaction was performed while formed water was distilled. Next, the pressure in the autoclave was gradually reduced from normal pressure to 3 kPa over 4 hours, and then heating was performed at 210° C. for 3 hours to distill off low boiling point substances, such as unreacted raw materials, and a glycolic acid oligomer (GAO) was obtained.

Determination Method of by-Products MGL and AAA and Sulfonic Acid Compounds PTS, MTS, and MSA The by-products MGL and AAA in the crude glycolide produced by the depolymerization reaction and the sulfonic acid compounds PTS, MTS, and MSA were determined by liquid chromatography (LC). Specifically, to 500 mg of a glycolide sample, 5 mL of 10 wt % sodium hydroxide aqueous solution was added and heated in an oil bath at 90° C. under stirring for 4 hours.

After cooling to room temperature, 2 mL of phosphoric acid was added, and it was confirmed that pH was from 1 to 3. Then, the mixture was diluted to adjust the volume to 50 mL. After the filtration by a filter, the mixture was injected into a liquid chromatography instrument, and MGL, AAA, PTS, MTS, and MSA were measured in the following conditions. The amounts of MGL, AAA, PTS, MTS, and MSA in the crude glycolide and presence or absence of these were determined.

LC Conditions

Measurement instrument: Lab Solutions, available from Shimadzu Corporation

DEGASS UNIT DGO-20A3R, available from Shimadzu Corporation

LIQUID CHROMATOGRAPH LC-20A, available from Shimadzu Corporation

COLUMN OVEN CTO-20AD, available from Shimadzu Corporation

AUTO SAMPLER SIL-20A, available from Shimadzu Corporation

Detector: UV/VIS DETECTOR SPD-20A ($\lambda$=210), available from Shimadzu Corporation Eluent: 0.1 M Ammonium dihydrogen phosphate+phosphoric acid [pH 2.5]

Column: Ultra AQ C18 150×4.6 mm×1 column, available from Restek Corporation; particle size=5 μm Column Temperature: 40° C.

Flow rate: 0.5 mL/min

Injection amount: 5 μL

Example 1

In a reactor having a volume of 0.5 L, 126 g of GAO, 130 g of tetraethylene glycol dibutyl ether, 100 g of octyltriethylene glycol (OTeG), and 163 mg of p-toluene sulfonic acid (PTS) (amount of 0.05 mass % relative to the total amount of the reaction solution) were added, and then heated to 235° C. to make the reaction system be a homogeneous solution.

After the depolymerization reaction was continued for 12 hours under reduced pressure of 3 kPa under heating at a temperature of 235° C. at an agitation rate of 170 rpm, the tetraethylene glycol dibutyl ether and the formed glycolide (hereinafter, referred to as "crude glycolide") were codistilled. Note that the recovery of the crude glycolide was performed every 1 hour, and GAO in an amount corresponding to 1.1-fold of the distilled crude glycolide was charged every hour during the depolymerization reaction. Then, using the recovered crude glycolide, the production rate and the production rate ratio of the by-products ("methyl glycolide (MGL)" and "acetoxyacetic acid (AAA)") in the crude glycolide and the total amount of distilled crude glycolide (GL) were determined. Furthermore, presence of PTS, which is a sulfonic acid-based compound, in the crude glycolide was determined. These results are shown in Table 1 and FIG. 1. Note that, in Table 1, "o" represents presence of the PTS or achievement of the effect of the thermal stabilizer, and "x" represents absence of the PTS or no achievement of the effect of the thermal stabilizer.

Example 2

The same operation as in Example 1 was performed except for using methyl p-toluenesulfonate (MTS) in place of the PTS. Then, in the same manner as in Example 1, the production rate and the production rate ratio of the by-products in the crude glycolide and the total amount of distilled crude glycolide were determined. Furthermore, presence of MTS, which is a sulfonic acid-based compound, in the crude glycolide was determined. These results are shown in Table 1 and FIG. 1.

Example 3

The same operation as in Example 1 was performed except for using methanesulfonic acid (MSA) in place of the PTS. Then, the production rate and the production rate ratio of the by-products in the crude glycolide and the total amount of distilled crude glycolide were determined. Furthermore, presence of MSA, which is a sulfonic acid-based compound, in the crude glycolide was determined. These results are shown in Table 1 and FIG. 1.

Example 4

Figure 2:
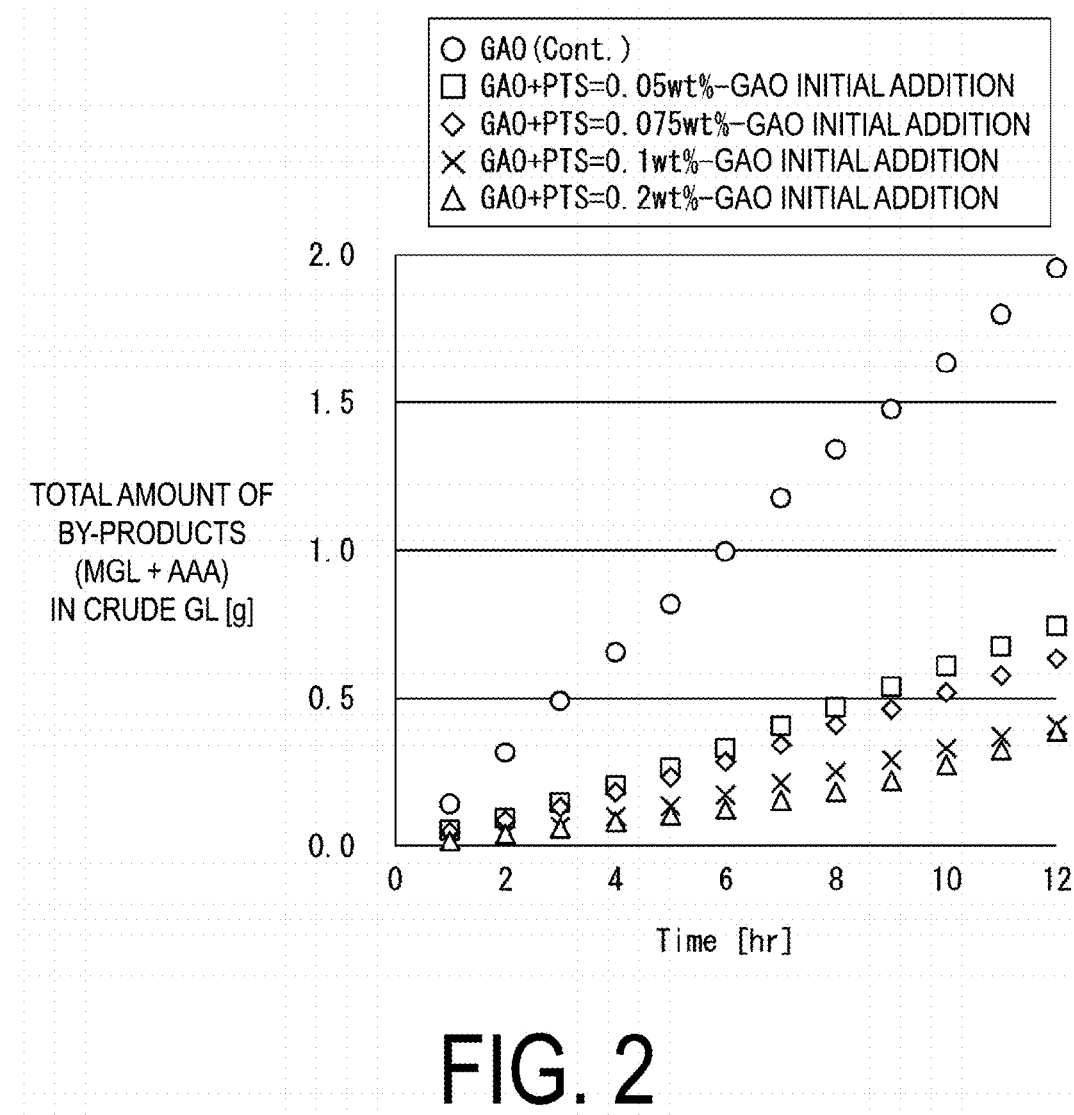
FIG. 2 is a graph showing a total amount of by-products (MGL+AAA) in a crude glycolide as a function of depolymerization reaction time.

The same operation as in Example 1 was performed except for adding 0.05 wt % of PTS, relative to the amount of the produced GAO, into glycolic acid during the GAO preparation and then adding no PTS in the following steps. Then, the distillation rate of the crude glycolide and the concentrations of MGL and AAA, which are by-products, in the crude glycolide were determined. Furthermore, presence of PTS, which is a sulfonic acid-based compound, in the crude glycolide was determined. These results are shown in Table 1 and FIG. 2.

Example 5

The same operation as in Example 1 was performed except for adding 0.075 wt % of PTS, relative to the amount of the produced GAO, into glycolic acid during the GAO preparation and then adding no PTS in the following steps. Then, the distillation rate of the crude glycolide and the concentrations of MGL and AAA, which are by-products, in the crude glycolide were determined. Furthermore, presence of PTS, which is a sulfonic acid-based compound, in the crude glycolide was determined. These results are shown in Table 1 and FIG. 2.

Example 6

Figure 3:
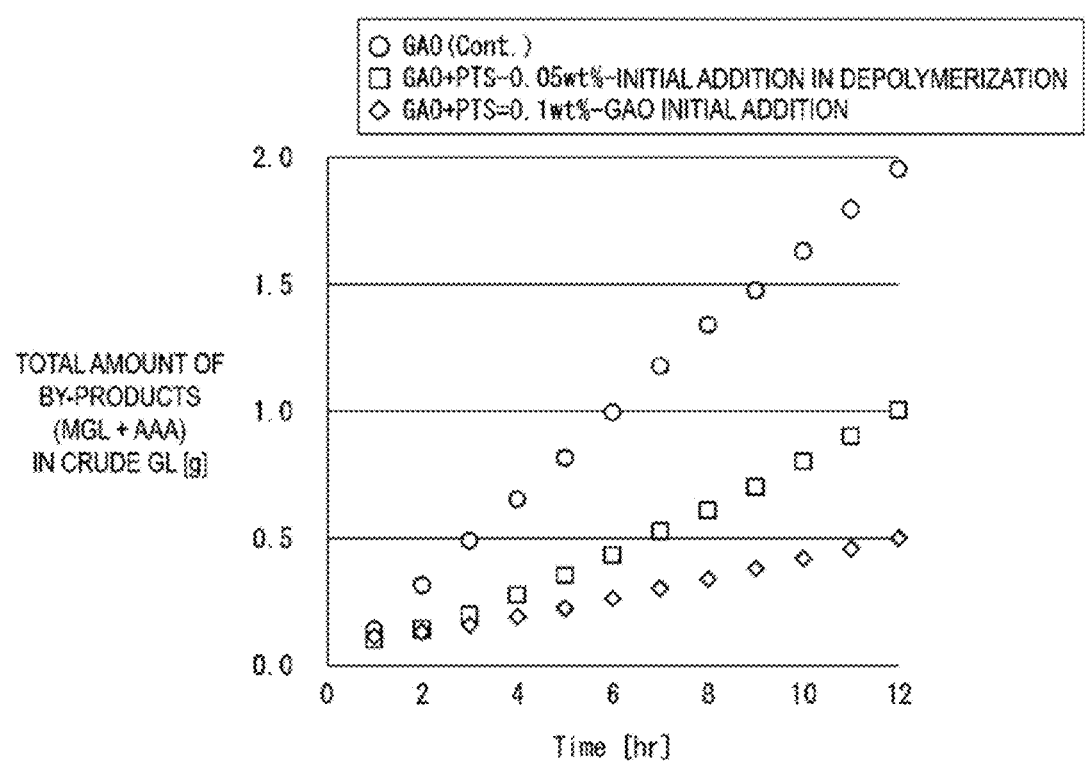
FIG. 3 is a graph showing a total amount of by-products (MGL+AAA) in a crude glycolide as a function of depolymerization reaction time.

The same operation as in Example 1 was performed except for adding 0.1 wt % of PTS, relative to the amount of the produced GAO, into glycolic acid during the GAO preparation and then adding no PTS in the following steps. Then, the distillation rate of the crude glycolide and the concentrations of MGL and AAA, which are by-products, in the crude glycolide were determined. Furthermore, presence of PTS, which is a sulfonic acid-based compound, in the crude glycolide was determined. These results are shown in Table 1 and FIGS. 2 to 3.

Example 7

Glycolide was produced in the same manner as in Example 1 was performed except for adding 0.2 wt % of PTS, relative to the amount of the produced GAO, into glycolic acid during the GAO preparation and then adding no PTS in the following steps. Then, the distillation rate of the crude glycolide and the concentrations of MGL and AAA, which are by-products, in the crude glycolide were determined. Furthermore, presence of PTS, which is a sulfonic acid-based compound, in the crude glycolide was determined. These results are shown in Table 1 and FIG. 2.

Example 8

In an autoclave having a volume of 20 L, 20 kg of a high purity 70% glycolic acid aqueous solution (available from The Chemours Company Fc, Llc), 136 g (amount corresponding to 0.14 mass % relative to the total amount of the produced glycolic acid oligomer) of dodecylbenzenesulfonic acid, and 4 g (amount corresponding to 0.004 mass % relative to the total amount of the produced glycolic acid oligomer) of iron as a depolymerization reaction catalyst were charged. Next, the mixture was heated under stirring at normal pressure to increase the temperature from room temperature to 210° C., and a polycondensation reaction was performed while formed water was distilled. Next, the pressure in the autoclave was gradually reduced from normal pressure to 3 kPa over 4 hours, and then heating was performed at 210° C. for 3 hours to distill off low boiling point substances, such as unreacted raw materials, and a glycolic acid oligomer was obtained.

In a reactor having a volume of 0.5 L, 126 g of glycolic acid oligomer, 130 g of tetraethylene glycol dibutyl ether, and 100 g of octyltriethylene glycol (OTeG) were added, and then heated to 235° C. to make the reaction system be a homogeneous solution.

After the depolymerization reaction was continued for 12 hours under reduced pressure of 3 kPa under heating at a temperature of 235° C. at an agitation rate of 170 rpm, the tetraethylene glycol dibutyl ether and the formed crude glycolide were codistilled. Note that the recovery of the crude glycolide was performed every 1 hour, and glycolic acid oligomer in an amount corresponding to 1.1-fold of the distilled crude glycolide was charged every hour during the depolymerization reaction. Then, from the recovered crude glycolide, the production rate and the production rate ratio of the by-products in the crude glycolide and the total amount of distilled crude glycolide (GL) were determined. Furthermore, presence of dodecylbenzenesulfonic acid, which is a sulfonic acid-based compound, in the crude glycolide was determined. These results are shown in Table 2. "The solubility in polyalkylene glycol diether" in Table 2 is a theoretical value at 25° C. as determined by applying a COSMO-RS (COnducor like Screening MOdel for Realistic Solvents) method.

Example 9

The same operation as in Example 8 was performed except for using 4-ethylbenzenesulfonic acid in place of dodecylbenzenesulfonic acid. Then, the production rate and the production rate ratio of the by-products in the crude glycolide and the total amount of distilled crude glycolide were determined. Furthermore, presence of 4-ethylbenzenesulfonic acid, which is a sulfonic acid-based compound, in the crude glycolide was determined. These results are shown in Table 2.

Example 10

The same operation as in Example 8 was performed except for using p-toluenesulfonic acid in place of the dodecylbenzenesulfonic acid. Then, the production rate and the production rate ratio of the by-products in the crude glycolide and the total amount of distilled crude glycolide were determined. Furthermore, presence of p-toluenesulfonic acid, which is a sulfonic acid-based compound, in the crude glycolide was determined. These results are shown in Table 2.

Example 11

The same operation as in Example 8 was performed except for using 2-naphthalenesulfonic acid in place of dodecylbenzenesulfonic acid. Then, the production rate and the production rate ratio of the by-products in the crude glycolide and the total amount of distilled crude glycolide were determined. Furthermore, presence of 2-naphthalenesulfonic acid, which is a sulfonic acid-based compound, in the crude glycolide was determined. These results are shown in Table 2.

Example 12

The same operation as in Example 8 was performed except for using 4-hydroxybenzenesulfonic acid in place of dodecylbenzenesulfonic acid. Then, the production rate and the production rate ratio of the by-products in the crude glycolide and the total amount of distilled crude glycolide were determined. Furthermore, presence of 4-hydroxybenzenesulfonic acid, which is a sulfonic acid-based compound, in the crude glycolide was determined. These results are shown in Table 2.

Comparative Example 1

The same operation as in Example 1 was performed except for adding no PTS. Then, in the same manner as in Example 1, the production rate and the production rate ratio of the by-products in the crude glycolide and the total amount of distilled crude glycolide were determined. Furthermore, presence of PTS, MTS, and MSA, which are sulfonic acid-based compounds, in the crude glycolide was determined. These results are shown in Table 1 and FIG. 1.

Comparative Example 2

The same operation as in Example 8 was performed except for adding no dodecylbenzenesulfonic acid. Then, in the same manner as in Example 8, the production rate and the production rate ratio of the by-products in the crude glycolide and the total amount of distilled crude glycolide were determined. Furthermore, presence of sulfonic acid-based compounds in the crude glycolide was determined. These results are shown in Table 2.

Reference Example

The same operation as in Example 8 was performed except for using sulfuric acid, which is an inorganic acid, in place of dodecylbenzenesulfonic acid. Then, in the same manner as in Example 8, the production rate and the production rate ratio of the by-products in the crude glycolide and the total amount of distilled crude glycolide were determined. Furthermore, presence of sulfuric acid in the crude glycolide was determined. These results are shown in Table 2.

TABLE 1

| | By-products in crude glycolide (MGL + AAA) | | Crude glycolide | | | |
|---|---|---|---|---|---|---|
| | Production rate [g/hr] | Production rate ratio (compared to Comparative Example 1) | Total distilled amount [g/12 hr] | Total distilled amount ratio (compared to Comparative Example 1) | Presence/absence of sulfonic acid-based compound in crude glycolide | Effect of thermal stabilizer |
| Example 1 | 0.10 | 0.63 | 203 | 0.9 | ○ | ○ |
| Example 2 | 0.13 | 0.81 | 220 | 1.0 | ○ | ○ |
| Example 3 | 0.08 | 0.50 | 216 | 1.0 | ○ | ○ |
| Example 4 | 0.06 | 0.38 | 220 | 1.0 | ○ | ○ |
| Example 5 | 0.05 | 0.31 | 220 | 1.0 | ○ | ○ |
| Example 6 | 0.04 | 0.25 | 219 | 1.0 | ○ | ○ |
| Example 7 | 0.04 | 0.25 | 220 | 1.0 | ○ | ○ |
| Comparative Example 1 | 0.16 | 1.00 | 221 | 1.0 | × | × |

TABLE 2

| | Sulfonic acid compound | Solubility in polyethylene glycol ether [mol/L] | By-products in crude glycolide (MGL + AAA) | |
|---|---|---|---|---|
| | | | Production rate [g/hr] | Production rate ratio (compared to Comparative Example 2) |
| Example 8 | Dodecylbenzenesulfonic acid | 0.380 | 0.0019 | 0.42 |
| Example 9 | 4-Ethylbenzenesulfonic acid | 0.135 | 0.0019 | 0.42 |
| Example 10 | p-Toluenesulfonic acid | 0.129 | 0.0019 | 0.42 |
| Example 11 | 2-Naphthalenesulfonic acid | 0.098 | 0.0017 | 0.39 |
| Example 12 | 4-Hydroxybenzenesulfonic acid | 0.048 | 0.0012 | 0.26 |
| Comparative Example 2 | Not added | | 0.0045 | 1.00 |
| Reference Example | Sulfuric acid | 0.355 | 0.0012 | 0.26 |

| | Crude glycolide | | Presence/absence of sulfonic acid-based compound or sulfuric acid in crude glycolide | Effect of thermal stabilizer |
|---|---|---|---|---|
| | Total distilled amount [g/12 hr] | Total distilled amount ratio (compared to Comparative Example 2) | | |
| Example 8 | 248 | 1.13 | ○ | ○ |
| Example 9 | 242 | 1.11 | ○ | ○ |
| Example 10 | 239 | 1.09 | ○ | ○ |
| Example 11 | 235 | 1.07 | ○ | ○ |
| Example 12 | 224 | 1.02 | ○ | ○ |

TABLE 2-continued

| | | | | |
|---|---|---|---|---|
| Comparative Example 2 | 219 | 1.00 | × | × |
| Reference Example | 219 | 1.00 | ○ | ○ |

From the results of Examples and Comparative Examples, it was found that production of by-products is suppressed without reduction of the distilled amount of the crude glycolide regardless of the structure of the sulfonic acid when the sulfonic acid compound is added as the thermal stabilizer.

Furthermore, it was found that the distilled amount of the crude glycolide in the systems that did not use a depolymerization catalyst (Examples 1 to 7) was substantially constant, with a range of the addition amounts of the sulfonic acid compounds shown in Examples. Meanwhile, it was found that the amount of the by-products in the crude glycolide was further suppressed when a larger amount of the sulfonic acid compound was added.

Furthermore, it was found that, while the timing of addition of the PTS, which is a sulfonic acid compound, did not affect the distilled amount of the crude glycolide, the suppression effect of the by-products was enhanced by adding the PTS during the synthesis of the glycolic acid oligomer.

Furthermore, it was found that, with the system in which the sulfonic acid compound and the depolymerization catalyst were used (Examples 8 to 12), in addition to the suppression of the by-product production, the distilled amount of the crude glycolide was increased. In particular, it was found that a greater solubility of the sulfonic acid compound in the polyalkylene glycol diether resulted in a greater distilled amount of the crude glycolide.

The invention claimed is:

1. A method for producing a cyclic ester, comprising:
    a step (I) of preparing a mixture (I) containing
    an aliphatic polyester,
    a polyalkylene glycol diether represented by Formula (1) below and having a boiling point from 230 to 450° C. and a molecular weight from 150 to 450,

(1)

wherein $R^1$ represents a methylene group or a linear or branched alkylene group having from 2 to 8 carbons, $X^1$ represents a hydrocarbon group, Y represents an alkyl group having from 2 to 20 carbons or an aryl group, p represents an integer of 1 or greater, and in a case where p is 2 or greater, a plurality of $R^1$ moieties may be the same or different, and
    a thermal stabilizer;
    a step (II) of producing a mixture (II) in a state of solution by heating the mixture (I) under normal pressure or reduced pressure to a temperature at which depolymerization reaction of the aliphatic polyester starts;
    a step (III) of producing a distillate (III) by continuing the heating of the mixture (II) and distilling a cyclic ester formed by the depolymerization reaction together with the polyalkylene glycol diether, and
    a step (IV) of recovering the cyclic ester from the distillate (III);
    wherein a polyalkylene glycol monoether represented by Formula (2) below is added to at least one of the mixture (I) and the mixture (II) as a solubilizing agent to enhance solubility of the aliphatic polyester in the polyalkylene glycol diether,

(2)

wherein $R^2$ represents a methylene group or a linear or branched alkylene group having from 2 to 8 carbons, $X^2$ represents a hydrocarbon group, r represents an integer of 1 or greater, and in the case where r is 2 or greater, a plurality of $R^2$ moieties may be the same or different; and
    wherein the thermal stabilizer is a sulfonic acid compound, a solubility of the sulfonic acid compound in the polyalkylene glycol diether is 0.04 mol/L or greater, and the distillate (III) further contains the thermal stabilizer.

2. The method for producing a cyclic ester according to claim 1, wherein, in the step (I), the thermal stabilizer is a sulfonic acid compound added in a proportion of 0.005 to 5.0 mass % relative to an amount of the aliphatic polyester.

3. The method for producing a cyclic ester according to claim 1, wherein the thermal stabilizer is a sulfonic acid compound used during preparation of the aliphatic polyester by heating an α-hydroxycarboxylic acid at a temperature of 100 to 250° C. under normal pressure or reduced pressure to perform a condensation reaction.

4. The method for producing a cyclic ester according to claim 1, wherein the mixture (I) further contains a depolymerization catalyst, and
    solubility of the thermal stabilizer in the polyalkylene glycol diether is 0.25 mol/L or greater.

* * * * *